(12) United States Patent
Jia et al.

(10) Patent No.: US 12,171,648 B2
(45) Date of Patent: Dec. 24, 2024

(54) FILTER

(71) Applicant: LIFETECH SCIENTIFIC (SHENZHEN) CO., LTD, Shenzhen (CN)

(72) Inventors: Xiaole Jia, Shenzhen (CN); Huiqiang Tang, Shenzhen (CN); Anning Li, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 420 days.

(21) Appl. No.: 16/956,782

(22) PCT Filed: Dec. 5, 2018

(86) PCT No.: PCT/CN2018/119275
§ 371 (c)(1),
(2) Date: Jun. 22, 2020

(87) PCT Pub. No.: WO2019/128652
PCT Pub. Date: Jul. 4, 2019

(65) Prior Publication Data
US 2020/0315769 A1    Oct. 8, 2020

(30) Foreign Application Priority Data

Dec. 26, 2017   (CN) .......................... 201711434036.0
Dec. 26, 2017   (CN) .......................... 201711437874.3

(51) Int. Cl.
A61F 2/01    (2006.01)

(52) U.S. Cl.
CPC ............ *A61F 2/012* (2020.05); *A61F 2/0108* (2020.05); *A61F 2/011* (2020.05);
(Continued)

(58) Field of Classification Search
CPC ........ A61F 2/0108; A61F 2/011; A61F 2/012; A61F 2002/013; A61F 2220/0008;
(Continued)

(56) References Cited

U.S. PATENT DOCUMENTS

| 6,443,972 B1 * | 9/2002 | Bosma | .................. A61F 2/0108 606/200 |
| 2009/0192543 A1 | 7/2009 | Wasdyke | |

(Continued)

FOREIGN PATENT DOCUMENTS

| CN | 101185582 A | 5/2008 |
| CN | 204909721 U * | 12/2015 |

(Continued)

OTHER PUBLICATIONS

International Search Report issued on Feb. 27, 2019 in corresponding International application No. PCT/CN2018/119275; 4 pages.
(Continued)

*Primary Examiner* — Kathleen S Holwerda
(74) *Attorney, Agent, or Firm* — Maier & Maier, PLLC

(57) ABSTRACT

A filter, including a main body part. The main body part includes a heart-proximal end, a plurality of connecting segments, and a first filter mesh connecting between the heart-proximal end and the plurality of connecting segments. An end of the connecting segments that is connected to the first filter mesh is bent towards a central longitudinal axis of the filter to form a bending part. A vertical distance between a proximal end of the bending part and the central longitudinal axis of the filter is less than a vertical distance between a distal end of the bending part and the central longitudinal axis of the filter.

18 Claims, 8 Drawing Sheets

(52) U.S. Cl.
CPC . *A61F 2002/016* (2013.01); *A61F 2220/0008* (2013.01); *A61F 2230/006* (2013.01); *A61F 2250/0029* (2013.01); *A61F 2250/0037* (2013.01)

(58) Field of Classification Search
CPC ........ A61F 2230/006; A61F 2250/0029; A61F 2250/0036
See application file for complete search history.

(56) References Cited

U.S. PATENT DOCUMENTS

| | | | |
|---|---|---|---|
| 2012/0143238 A1* | 6/2012 | Sogard | A61F 2/0105 606/200 |
| 2013/0006295 A1* | 1/2013 | Chanduszko | A61F 2/0108 606/200 |
| 2013/0035713 A1 | 2/2013 | Snow | |
| 2013/0226224 A1* | 8/2013 | Snow | A61F 2/0105 606/200 |

FOREIGN PATENT DOCUMENTS

| | | |
|---|---|---|
| CN | 106308974 A | 1/2017 |
| CN | 206534731 U | 10/2017 |
| CN | 206630733 U | 11/2017 |
| WO | 0211812 A1 | 2/2002 |
| WO | 03/002032 A2 | 1/2003 |

OTHER PUBLICATIONS

Chinese Office Action issued on May 6, 2021, in connection with corresponding CN Application No. 201711437874.3 (17 pp., including machine-generated English translation).

Extended European Search Report issued on Feb. 4, 2021, in connection with corresponding EP Application No. 18897532.0; 7 pages.

Chinese Office Action issued on Jul. 31, 2020, in connection with corresponding CN Application No. 201711434036.0 (13 pp., including machine-generated English translation).

* cited by examiner

FILTER

FIELD

The embodiments relate to an implanted medical instrument, and in particular to a filter.

BACKGROUND

Pulmonary embolism (PE) is a common disease, with high mortality. According to statistics, the mortality of PE without treatment is 20%-30%, and the new cases account for 0.2% of the population every year. There are about 2.7 million new patients per year calculated from 1.35 billion population in China.

A vena cava filter (hereinafter referred to as "filter") has been clinically proven to reduce the incidence of pulmonary embolism. Permanent implantation of the filter carries the following risks: long-term contact of the filter with blood and vascular endothelium may lead to protein adsorption, platelet adhesion, and ultimately thrombosis resulting in venous blockage, or pulmonary embolism recurrence; for long-term implantation in vivo, there may be risks of filter deformation, tilt, shift, fracture, and even penetration through blood vessels. Therefore, it is clinically recommended to use a temporary filter which is implanted during the acute phase of a patient's deep venous thrombosis and then removed after the acute phase when the risk of thrombosis shedding is reduced.

After the implantation of the vena cava filter into the inferior vena cava for a certain period of time, a support rod of the filter will be crawled and wrapped by endothelial cells to varying degrees, which may damage the intima of blood vessels during the removal, therefore, it is necessary to provide a filter which can be removed conveniently without damaging the intima of the blood vessels.

SUMMARY

A problem to be solved is to provide a filter so as to solve the defect in the prior art that the filter is inconveniently removed when being implanted into a blood vessel.

A solution adopted for solving the problem is as follows.

A filter is provided, including a main body part. The main body part includes a heart-proximal end, a plurality of connecting segments and a first filter mesh connected between the heart-proximal end and the plurality of connecting segments. One end of the connecting segments that is connected to the first filter mesh is bent towards one side of a longitudinal center axis of the filter to form a bending part, and a vertical distance between the proximal end of the bending part and the longitudinal center axis of the filter is less than a vertical distance between the distal end of the bending part and the longitudinal center axis of the filter.

A filter is provided, including a main body part and a plurality of support parts. The support parts include at least one support which includes a guide segment connected to the main body part of the connector. Under the natural release state of the filter, an included angle between a connecting line between both ends of the guide segment and the longitudinal center axis of the filter is 20°-85°, and the ratio of a height of the support in the radial direction of the filter to the maximum distance of the support to the longitudinal center axis of the filter is ⅛-⅓.

Implementing a filter of the embodiments has the following beneficial effects: the embodiments are provided with the bending part by bending an end of the connecting segments that is connected to the first filter mesh towards one side of the longitudinal center axis of the filter, allowing a surface of the first filter mesh to be away from a surface of a blood vessel so as to avoid contacting an inner wall of the blood vessel when the first filter mesh bulge, and further the bending part can bear a portion of stress, thereby preventing stress from concentrating on a connection between the first filter mesh and the connecting segments. Further, compared with a straight connecting segment, the bending part provided on the connecting segments can also increase the length of the connecting segments, delay the time for the endothelial tissue to climb to the first filter mesh, and increase the climbing difficulty of endothelial cells.

BRIEF DESCRIPTION OF THE DRAWINGS

The embodiments will now be further described with reference to the accompanying drawings and embodiments, in which.

DETAILED DESCRIPTION OF THE EMBODIMENTS

In order that the features, objects, and effects of the embodiments may be more clearly understood, specific embodiments thereof will now be described in detail with reference to the accompanying drawings.

It should be noted that when an element is referred to as being "secured" to another element, it may be directly on another element or intervening elements may also be present. When an element is referred to as being "connected" to another element, it may be directly connected to another element or intervening elements may be present. As used herein, the terms "perpendicular", "horizontal", "left", "right", "upper", "lower", "distal", "proximal", and the like are used for descriptive purposes only.

In the field of filters, the section of the filter that is closer to the heart after implantation in a human body is called the heart-proximal end, and the end that is farther from the heart is called the heart-distal end.

Figure 1:
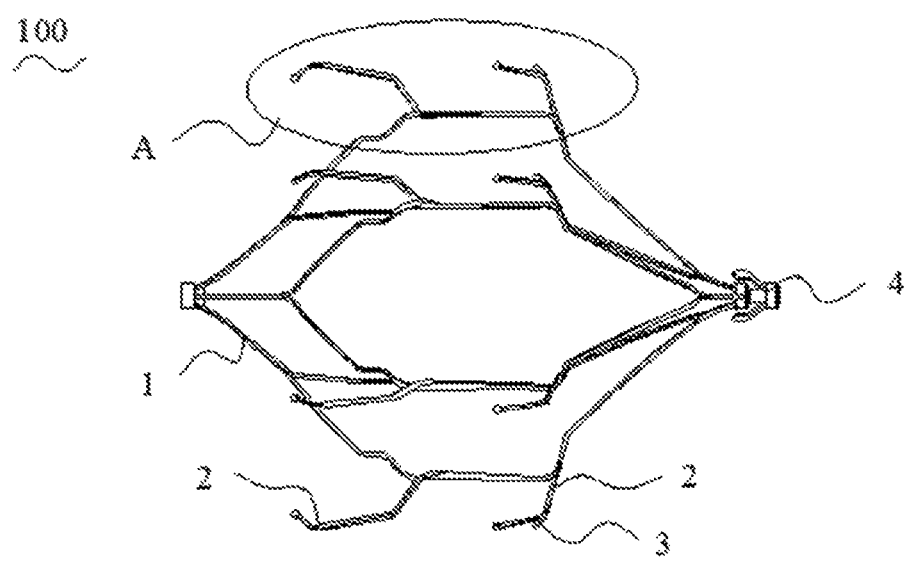
FIG. 1 is a structural schematic diagram of a filter according to an embodiment

As shown in FIG. 1, one of the embodiments provides a filter 100 for implantation into a lumen of a human body, to capture thrombus in the lumen, includes a main body part 1, a plurality of support parts 2 connected to the main body part 1, at least one mooring anchor 3 connected to the support parts 2, and a recovery hook 4 provided on one end of the main body part 1.

Figure 2:
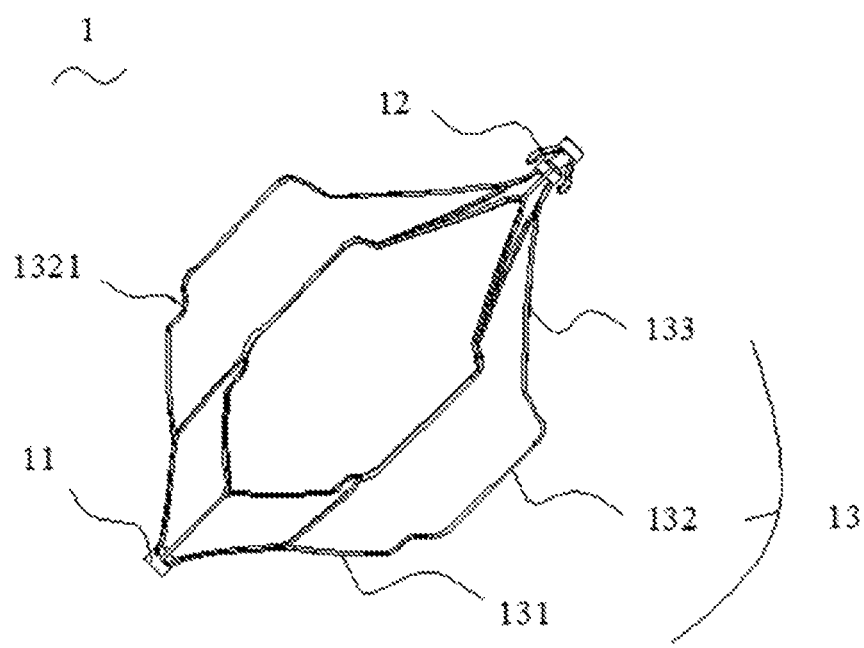
FIG. 2 is a stereogram of a main body part of the filter shown in FIG. 1.

Referring to FIG. 2, the main body part 1 includes a heart-proximal end 11, a heart-distal end 12, and a connector 13 provided between the heart-proximal end 11 and the heart-distal end 12. The connector 13 includes a first filter mesh 131, a second filter mesh 133, and a plurality of connecting segments 132 between the first filter mesh 131 and the second filter mesh 133, and the plurality of connecting segments 132 are equally spaced along the circumferential direction of the connector 13. The first filter mesh 131 is a mesh structure, and the first filter mesh 131 extends from one end of the plurality of connecting segments 132 towards a direction away from the connecting segments 132, and the first filter mesh 131 converges to the heart-proximal end 11, and the second filter mesh 133 is a mesh structure, and the second filter mesh 133 extends from the other end of the plurality of connecting segments 132 towards a direction away from the connecting segments 132, and the second filter mesh 133 converges to the heart-distal end 12.

Figure 3:
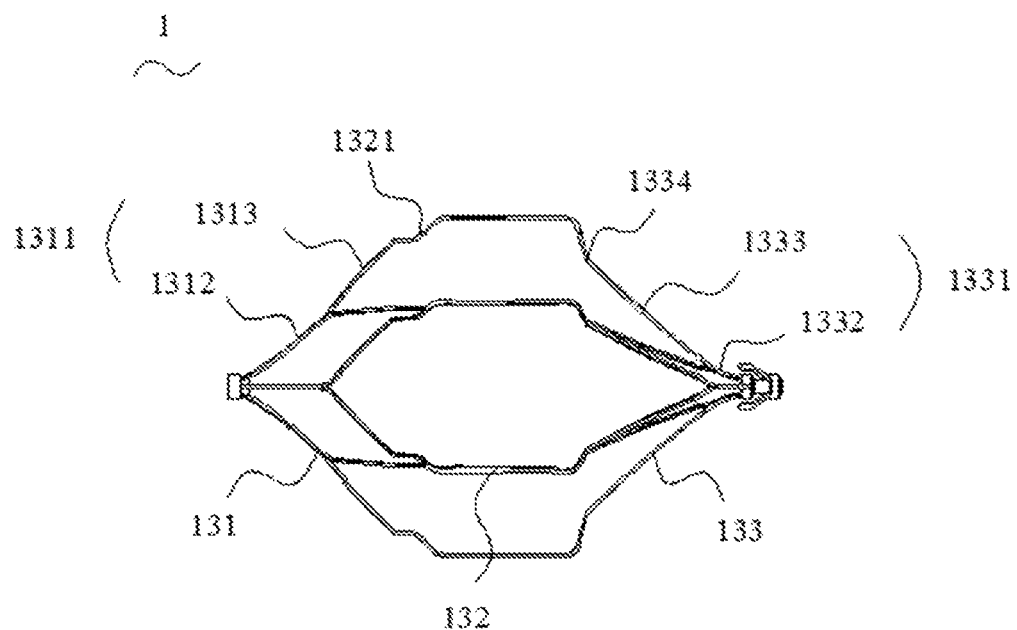
FIG. 3 is a front view of the main body part of the filter shown in FIG. 1.

Referring to FIG. 3, the first filter mesh 131 is composed of a set of first Y-shaped rods 1311 equally spaced along the circumferential direction of the connector 13, the number of the first Y-shaped rods 1311 corresponding to the number of the connecting segments 132, each of the first Y-shaped rods 1311 including a first main branch segment 1312 and two first branch segments 1313 separated by one end of the first main branch segment 1312. The first main branch segment 1313 is connected between the heart-proximal end 11 and the two first branch segments 1313, and the ends, away from the heart-proximal end 11, of two adjacent first branch segments 1313 of two adjacent first Y-shaped rods 1311 converge on one connecting segment 132. It can be noted that the end, close to the heart-proximal end 11, of the first main branch segment 1312 is the proximal end of the first filter mesh 131, and the end, away from the heart-proximal end 11, of each first branch segment 1313 of the first Y-shaped rods 1311 is the distal end of the first filter mesh 131.

The second filter mesh 133 is composed of a set of second Y-shaped rods 1331 equally spaced along the circumferential direction of the connector 13, the number of the second Y-shaped rods 1331 being half of the number of the connecting segments 132. Each second Y-shaped rods 1331 includes a second main branch segment 1332 and two second branch segments 1333 separated by one end of the second main branch segment 1332. The second main branch segment 1333 is connected between the heart-distal end 12 and the two second branch segments 133, and each second branch segments 1333 of the second Y-shaped rods 1331 is connected to one connecting segment 132. It can be noted that the part, close to the heart-distal end 12, of the second main branch segment 1332 is the distal end of the second filter mesh 133, and the end, away from the heart-distal end 12, of each second branch segment 1333 of the second Y-shaped rods 1331 is the proximal end of the second filter mesh 133.

As can be seen from the above, the main body part 1 of the filter 100 has an asymmetric structure as a whole, and the number of the first Y-shaped rods 1311 is twice the number of the second Y-shaped rods 1331, that is, the rod density of the first filter mesh 131 is greater than the rod density of the second filter mesh 133.

It can be noted that the connector 13 is made of a material having a shape memory function, such as nitinol, and is deformed to an expanded state after the filter 100 is conveyed to the lumen of a human body and released from a conveying sheath of a conveyor. In the process of thrombus filtration, blood flow flows from the heart-distal end 12 to the heart-proximal end 11, thrombus first passes through a gap formed by the second Y-shaped rods 1331 with a smaller rod density, enters the inside of the filter 100, and is then blocked by the first Y-shaped rods 1311 with a larger rod density to be retained inside the filter 100, thereby achieving the filtration of thrombus. The recovery hook 4 can be selectively provided at the heart-proximal end 11 or the heart-distal end 12, and the recovery hook 4 can be in a hook body or a threaded structure and the like and is used for removing the filter 100 after thrombus filtration.

Figure 4:
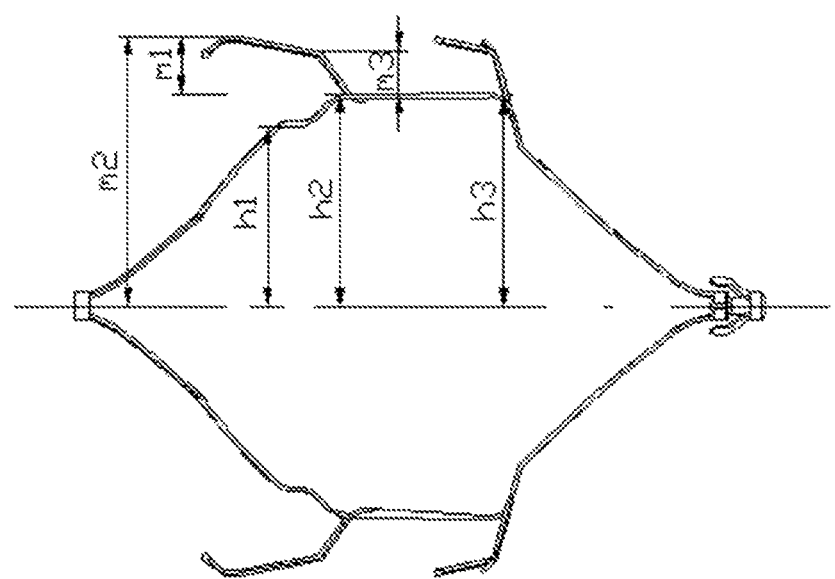
FIG. 4 is structural schematic diagram of a distance from the proximal end and the distal end of a bending part to the longitudinal center axis of the filter shown in FIG. 1.

As shown in FIGS. 3 and 4, one end of the connecting segments 132 that is connected to the first filter mesh 131 is bent towards one side of the longitudinal center axis of the filter 100 to form a bending part 1321. A vertical distance h1 between the proximal end of bending part 1321 and the longitudinal center axis of the filter 100 is less than a vertical distance h2 between the distal end of the bending part 1321 and the longitudinal center axis of the filter 100. The proximal end of the bending part 1321 herein refers to the end of the bending part 1321 that is connected to the first filter mesh 131, and the distal end of the bending part 1321 refers to the end of the bending part 1321 that is away from the first filter mesh 131.

When the filter 100 is implanted into the lumen, the lumen wall has a radially inward pressure on the filter 100 causing the connecting segments 132 to move towards one side of the longitudinal center axis of the filter 100, and the portion of the first filter mesh 131 that is close to the connecting segments 132 will bulge upward against the inner wall of the blood vessel under a reaction force, causing vascular endothelium to climb to the bulge, which is detrimental to the recovery of the filter 100. Further, when the first filter mesh 131 bulges upward, an included angle between the two first branch segments 1313 converging on one connecting segment 132 becomes large, resulting in stress concentration on a connection between the two first branch segments 1313 and the connecting segments 132. Due to the diastolic function of the blood vessel, the pressure acting on the support parts 2 by the lumen wall is an alternating stress, and under the action of the alternating stress, the two first branch segments 1313 of the first filter mesh 131 converging on one connecting segment 132 are prone to fatigue fracture after a long time of operation.

According to the embodiments, the bending part 1321 is provided at one end, connected to the first filter mesh 131, of the connecting segments 132, allowing a surface of the first filter mesh 131 to be away from a surface of the blood vessel so as to avoid contacting an inner wall of the blood vessel when the first filter mesh 131 bulges, and the lowest point of the bending part 1321 can pull the distal end of the first filter mesh 131 to move towards one side of the longitudinal center axis of the filter 100 so as to transfer the bulging position on the first filter mesh 131 from the distal position of the first filter mesh 131 to the middle or proximal position of the first filter mesh 131, thereby preventing stress from concentrating on a connection of the two first branch segments 1313 and the connecting segments 132. As used herein, the lowest point of the bending part 1321 refers to the point on the bending part 1321 that is the shortest perpendicular distance from the longitudinal center axis of the filter 100. Further, by providing the bending part 1321 at the end where the connecting segments 132 are connected to the first filter mesh 131, the bending part 1321 can bear a portion of the stress and reduce the stress concentrated on the connection between the two first branch segments 1313 and the connecting segments 132. Compared with a straight connecting segment 132, the bending part 1321 provided on the connecting segments 132 can also increase the length of the connecting segments 132, delay the time for the endothelial tissue to climb to the first filter mesh 131, and increase the difficulty for endothelial cells to climb to the first filter mesh 131.

It can be appreciated that when the vertical distance h1 between the proximal end of the bending part 1321 and the longitudinal center axis of the filter 100 is too small, the area of the first filter mesh 131 projected onto a plane perpendicular to the longitudinal center axis of the filter 100 is small, resulting in a reduced ability of the filter 100 to capture thrombus. However, if the distance at which the proximal end of the bending part 1321 is folded down is too small, it is of little significance to provide the bending part 1321, therefore the height difference between the vertical distance h1 between the proximal end of the bending part 1321 and the longitudinal center axis of the filter 100 and the vertical distance h2 between the distal end of the bending part 1321 and the longitudinal center axis of the filter 100 is 1 mm-5 mm, for example 2 mm-3 mm.

Figure 5:
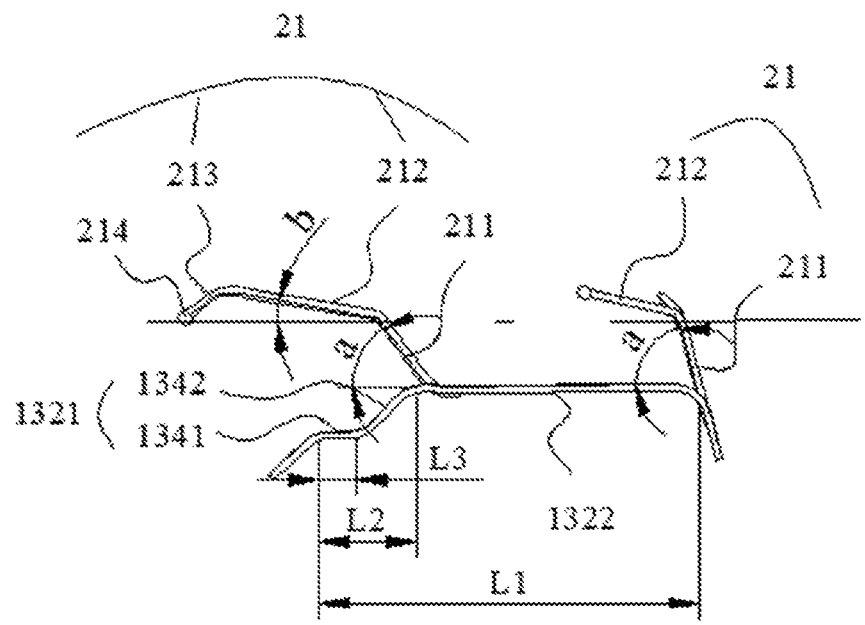
FIG. 5 is an enlarged view of portion A of the filter shown in FIG. 1.

With reference to FIG. 5, in a case where the height difference between the proximal end of the bending part 1321 and the distal end of the bending part 1321 in the radial direction of the filter 100 is constant, the shorter a distance L2 between the proximal end of the bending part 1321 and the distal end of the bending part 1321 in a direction of the longitudinal center axis of the filter 100 is, the greater an included angle between a connecting line between the proximal end of the bending part 1321 and the distal end of the bending part 1321 and the longitudinal center axis of the filter 100 is, which may affect the compliance of the filter 100 into and out of a sheath. However, when L2 is too long, it may result in poor stability and easy tilting of the filter 100. Therefore, the ratio of the distance L2 between the proximal end of the bending part 1321 and the distal end of the bending part 1321 in the direction of the longitudinal center axis of the filter 100 to the distance L1 between both ends of the connecting segments 132 in the direction of the longitudinal center axis of the filter 100 is 1/20-3/5, for example 1/10-1/3.

The connecting segments 132 include the bending part 1321 and a connecting part 1322 which are connected, and in this embodiment the connecting part 1322 is distributed substantially parallel to the longitudinal center axis of the filter 100. The bending part 1321 includes a first bending segment 1341 and a second bending segment 1342 which are connected, the first bending segment 1341 being connected to the distal end of the first filter mesh 131, the second bending segment 1342 being connected to the proximal end of the connecting part 1322. In order to avoid stress concentration, the first bending segment 1341 is smoothly connected to the first filter mesh 131, the first bending segment 1341 to the second bending segment 1342, and the second bending segment 1342 to the connecting part 1322. It can be appreciated that when a distance L3 between both ends of the first bending segment 1341 in the direction of the longitudinal center axis of the filter 100 is too short, it tends to cause stress to be concentrated at the distal end of the first filter mesh 131, but if L3 is too long, it affects the compliance of the filter 100 into and out of the sheath. Therefore, the ratio of the distance L3 between both ends of the first bending segment 1341 in the direction of the longitudinal center axis of the filter 100 to the distance L2 between both ends of the bending part 1321 in the direction of the longitudinal center axis of the filter 100 is 1/5-3/5, for example 1/4-1/3.

It can be appreciated that the embodiments do not limit the particular configuration of the bending part 1321, and in other embodiments, the first bending segment 1341 and the second bending segment 1342 may be straight segments, curved segments, or hybrid segments in which the straight segments are connected to the curved segments. The lowest point of the bending part 1321 may be at the proximal end of the bending part 1321 or at the middle of the bending part 1321. Alternatively, in other embodiments, the bending part 1321 includes three or more bending segments with a smooth connection between the three or more bending segments. For example, the first bending segment 1341 is a straight segment parallel to the direction of the longitudinal center axis of the filter 100 to facilitate processing.

Figure 6:
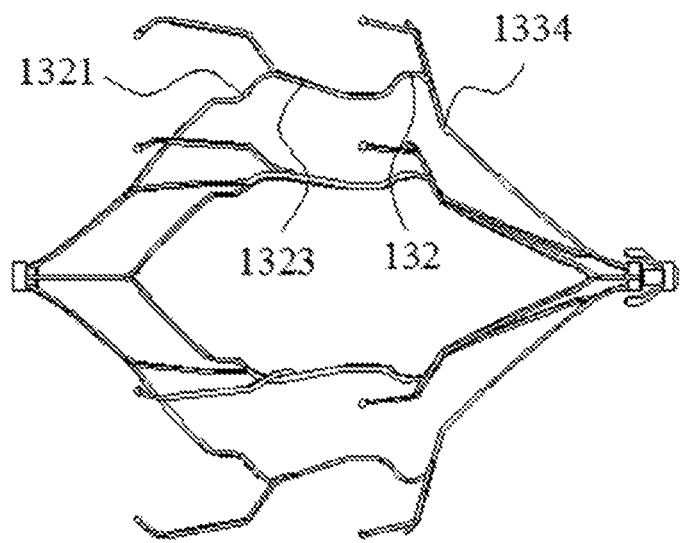
FIG. 6 is a structural schematic diagram that a concave structure is provided on a connecting part of the filter shown in FIG. 1.

It can be further appreciated that the embodiments do not limit the specific configuration of the connecting part 1322, and, in other embodiments, the connecting part 1322 may be a straight segment, a curved segment, or a combination of straight and curve segments disposed obliquely with respect to the direction of the longitudinal center axis of the filter 100. For example, referring to FIG. 6, the connecting part 1322 is provided with a concave structure 1323 that is designed to keep most of the surface of the connecting segments 132 away from the surface of the blood vessel, thereby further increasing the climbing difficulty of endothelial cells.

Referring to FIG. 4, a vertical distance h3 between the distal end of the connecting part 1322 and the longitudinal center axis of the filter 100 is not less than the vertical distance h1 between the proximal end of the bending part 1321 and the longitudinal center axis of the filter 100, and is not greater than the vertical distance h2 between the distal end of the bending part 1321 and the longitudinal center axis of the filter 100. The distal end of the connecting part 1322 herein refers to the end of the connecting part 1322 that is connected to the second filter mesh 133. If h3 is less than h1, the area of the second filter mesh 133 projected onto a plane perpendicular to the longitudinal center axis of the filter 100 is small, resulting in a reduced ability of the filter 100 to capture thrombus; if h3 is greater than h2, it may result in poor stability and easy tilting of the filter 100. For example, the vertical distance h3 between the distal end of the connecting part 1322 and the longitudinal center axis of the filter 100 is equal to the vertical distance h2 between the distal end of the bending part 1321 and the longitudinal center axis of the filter 100.

Further, as shown in FIG. 3, the second branch segments 1333 of the second filter mesh 133 are provided with a flexible part 1334 bent towards one side of the longitudinal center axis of the filter 100, and a bending strength of the second filter mesh 133 at the flexible part 1334 is lower than a bending strength of the second filter mesh 133 at the remaining area except the flexible part 1334. When the filter 100 is radially extruded, the flexible part 1334 is bent and deformed towards one side of the longitudinal center axis of the filter 100, allowing a surface of the second filter mesh 133 to be away from a surface of the blood vessel so as to avoid contacting an inner wall of the blood vessel when the second filter screen 133 bulges, delay the time for the endothelial tissue to climb to the second filter mesh 133, and increase the climbing difficulty for the endothelial cells to climb to the second filter mesh 133.

As shown in FIG. 1, one end of each support part 2 is connected to the main body part 1, and the other end thereof extends towards one side of the heart-proximal end 11. After the filter 100 with the support parts 2 is implanted into the lumen of a human body, the support parts 2 are directly contacted with the inner wall of the lumen, and the main body part 1 is separated from the inner wall of the lumen, so that when the filter 100 is removed, the support parts 2 only need to be separated from the lumen wall. Since the contact surface between the support parts 2 and the lumen wall is small, the stimulation to the lumen wall can be reduced to facilitate the removal of the filter 100. Further, by providing the support parts 2, it is possible to further delay the time for the endothelial tissue to climb to the first filter mesh 131 and the connecting segments 132, and to extend the recovery time of the filter.

Figure 7:
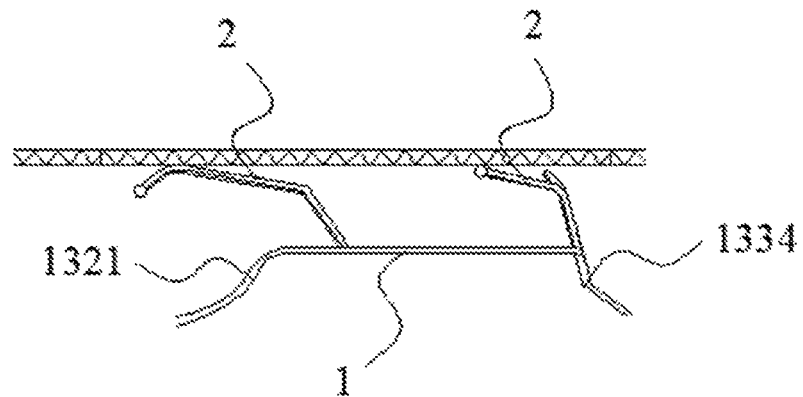
FIG. 7 is a structural schematic diagram that the filter shown in FIG. 1 is placed in a blood vessel.
Figure 8:
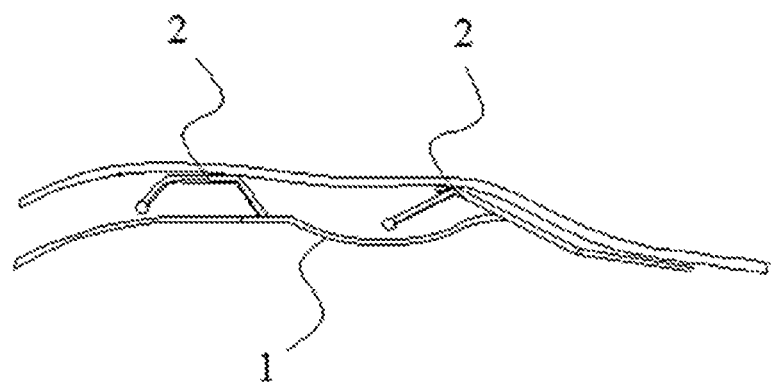
FIG. 8 is a structural schematic diagram that the filter in the prior art is placed in a blood vessel.

When the filter 100 is implanted in the lumen, the lumen wall has a radially inward pressure on the filter 100, by providing the bending part 1321 on the connecting segments 132 and the flexible part 1334 on the second filter mesh 133, the bending part 1321 and the flexible part 1334 are able to bend and deform towards one side of the longitudinal center axis of the filter 100 when the support parts 2 are subjected to pressure from the radial direction of the filter 100, so that the support parts 2 are kept in a straight deformation all the time. FIG. 7 is a deformation schematic diagram after the filter 100 of the embodiment is implanted into a blood vessel, and FIG. 8 is a deformation schematic diagram after the filter 100 not provided with the bending part 1321 and the flexible part 1334 is implanted into a blood vessel. By comparing FIG. 7 and FIG. 8, it can be apparent that after the filter 100 in FIG. 7 is implanted into the blood vessel, the bending part 1321 and the flexible part 1334 deform so as to make the support parts 2 keep straight deformation and prevent a connection between the support parts 2 and the connecting segments 132 from bulging to contact the vessel wall, so that the filter is more stable in the blood vessel, while the connection between the support parts 2 and the connecting segments 132 in FIG. 8 is prone to bulge to contact the vessel wall.

Figure 9:
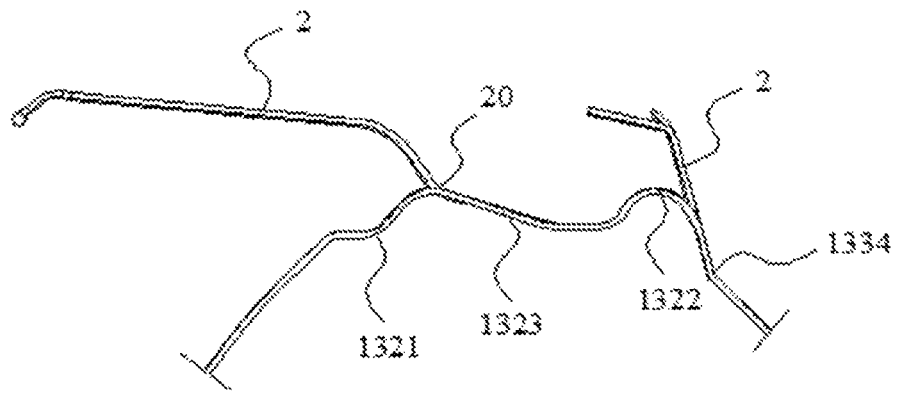
FIG. 9 is a structural schematic diagram that support parts of the filter shown in FIG. 1 is provided on the connecting part.
Figure 10:
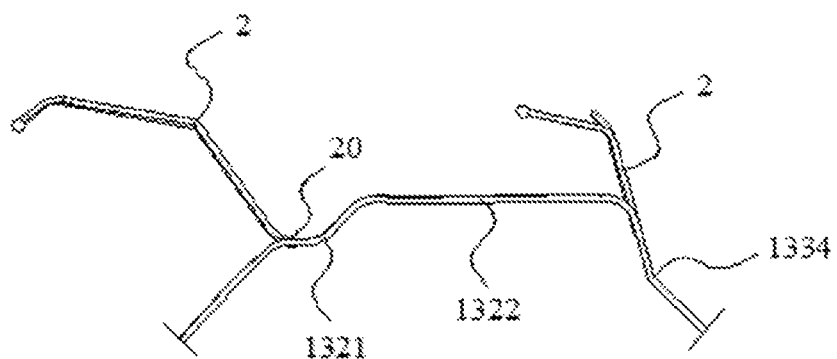
FIG. 10 is a structural schematic diagram that the support parts of the filter shown in FIG. 1 is provided on the bending part.
Figure 11:
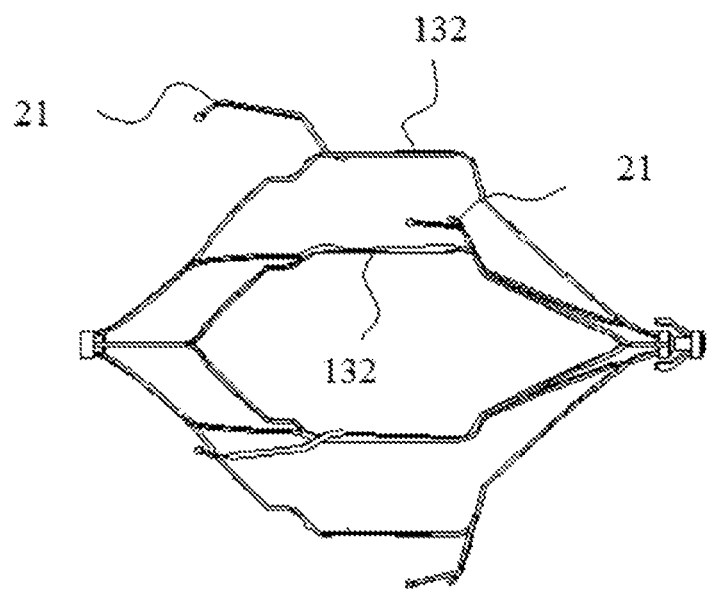
FIG. 11 is a structural schematic diagram that a support part is provided on a connecting segment of the filter shown in FIG. 1.

It can be appreciated that the embodiments do not limit the specific location of the support parts 2 on the connecting segments 132, and as shown in FIG. 9, an intersection point 20 of the support parts 2 and the connecting segments 132 is located on the connecting part 1322. Alternatively, as shown in FIG. 10, the intersection point 20 of the support parts 2 and the connecting segments 132 is located in the bending part 1321. It can also be appreciated that the embodiments do not limit the specific number of the support parts 2 on each connecting segment 132 to which one or more support parts 2 may be connected. As shown in FIG. 11, only one support part 2 is connected to each connecting segment 132, and the support parts 2 on two adjacent connecting segments 132 are staggered.

Figure 12:
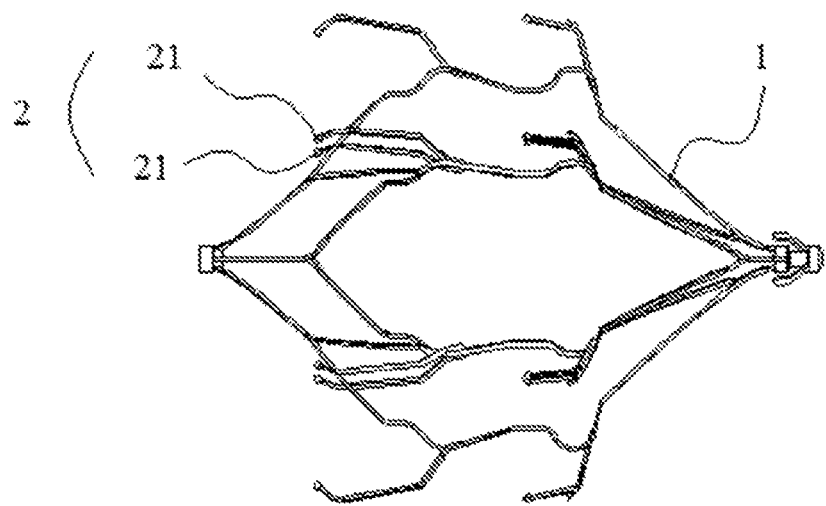
FIG. 12 is a structural schematic diagram that two supports are provided on the support parts of the filter shown in FIG. 1.

Referring to FIG. 12, each support part 2 includes at least one support 21. Referring to FIG. 5, each support 21 includes a guide segment 211 and a support segment 212 connected to the guide segment 211, and the guide segment 211 is smoothly connected to the support segment 212.

One end of the guide segment 211 is connected to the connecting segments 132, the other end of the guide segment 211 extends radially outward in a direction away from the recovery hook 4, and under the natural release state of the filter, an included angle a between a connecting line between both ends of the guide segment 211 and the longitudinal center axis of the filter 100 is 20°-85°. With reference to FIG. 4, the ratio of a height m1 of the support 21 in the radial direction of the filter to a maximum distance m2 between the support 21 and the longitudinal center axis of the filter 100 is ⅛-⅓. The height m1 of the support 21 in the radial direction of the filter herein refers to the distance between the highest point of the support 21 and the intersection point 20 of the support 21 and the connecting segments 132 in the radial direction of the filter.

It can be appreciated that when the outer diameter of the filter 100 is specified, if the height m1 of the support 21 in the radial direction of the filter 100 is too large, not only is the support 21 easily bent with a poor support effect, but also the corresponding outer diameter of the main body part 1 is smaller, affecting the thrombus filtration effect of the filter 100; if the height m1 of the support 21 in the radial direction of the filter 100 is too small, the endothelial tissue easily climbs to the main body part 1, which is detrimental to the recovery of the filter 100. In the case where the height m1 of the support 21 in the radial direction of the filter 100 is constant, if an included angle a between the connecting line between both ends of the guide segment 211 and the longitudinal center axis of the filter 100 is too large, it may affect the compliance of the filter 100 into and out of the sheath, and if the included angle a is too small, it may affect the support effect of the support 21. According to the embodiments, by adjusting the ratio of the height m1 of the support 21 in the radial direction of the filter 100 to the maximum distance m2 between the support 21 and the longitudinal center axis of the filter 100, and by adjusting the included angle a between the connecting line between both ends of the guide segment 211 and the longitudinal center axis of the filter 100, the support 21 has a better supporting force and the time of endothelial climbing is delayed without affecting the effect of filtering thrombus by the filter 100. For example, the included angle a between the connecting line between both ends of the guide segment 211 and the longitudinal center axis of the filter 100 is 30°-60°, and the ratio of the height m1 of the support 21 in the radial direction of the filter to the maximum distance m2 between the support 21 to the longitudinal center axis of the filter 100 is ⅙-5/18.

In this embodiment, one end of the support segment 212 is connected to the guide segment 211, the other end of the support segment 212 extends radially outward in a direction away from the recovery hook 4, and an included angle b between a connecting line between both ends of the support segment 212 and the longitudinal center axis of the filter 100 is 10°-20°, and the ratio of the height m3 of both ends of the guide segment 211 in the radial direction of the filter to the height m1 of the support 21 in the radial direction of the filter 100 is ½-⅚. When the height m3 is constant, if the included angle b is too large, the distance between both ends of the support segment 212 in the direction of the longitudinal center axis of the filter 100 is too short, the contact area between the support segment 212 and the lumen wall is small, causing large stimulation on the lumen wall, and if the included angle b is too small, the support segment 212 moves towards one side of the longitudinal center axis of the filter 100 under the action of the pressure of the lumen wall, so that a connection between the guide segment 211 and the support segment 212 bulges to contact the lumen wall and easily pierce the vessel wall.

Figure 13:
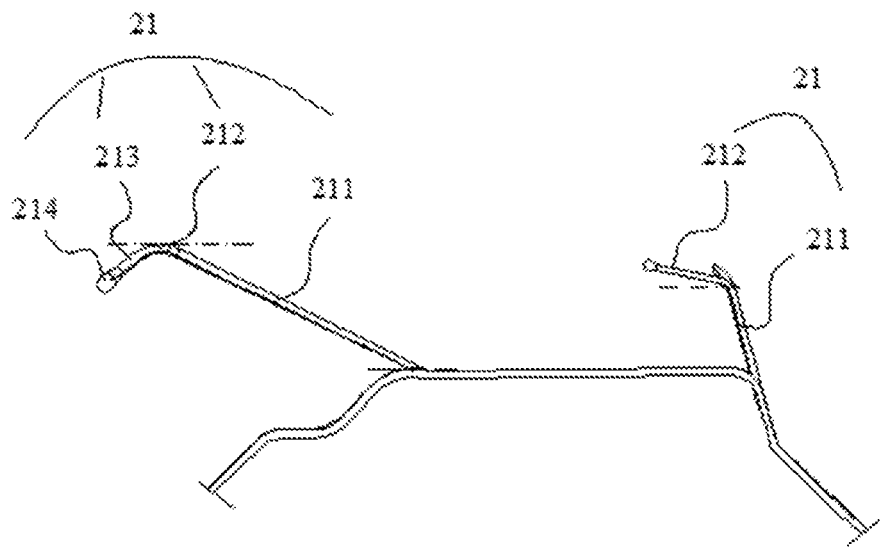
FIG. 13 is a schematic diagram that a support segment of the support parts of the filter shown in FIG. 1 is circular arc structure.

It can be appreciated that the embodiments do not limit the particular configuration of the support segment 212, and in other embodiments, the support segment 212 may be other configurations. As shown in FIG. 13, the support segment 212 has a circular arc structure.

The support 21 may also include a lower folding segment 213 smoothly connected to the support segment 212, and the lower folding section 213 is bent and extends towards one side of a longitudinal centerline of the filter 100. It can be appreciated that when an included angle between the lower folding segment 213 and the longitudinal centerline of the filter 100 is greater, the lower folding segment 213 tends to puncture the vessel wall, and when the included angle between the lower folding segment 213 and the longitudinal centerline of the filter 100 is smaller, the into and out sheath force is affected, therefore the included angle between the lower folding segment 213 and the longitudinal centerline of the filter 100 is for example 20°-75°. Further, the terminal of the lower folding segment 213 is provided with a spherical part 214 with a smooth outer contour to prevent the support segment 212 from piercing the vessel wall.

In this embodiment, each support part 2 includes a support 21 located on one side of the connecting segments 132. It can be appreciated that in other embodiments, as shown in FIG. 12, each support part 2 may also include two or more supports 21 connected to each side of the connecting segments 132. It can be appreciated that when two or more supports 21 are provided on each connecting segment 132, the structure of the two or more supports 21 may be the same or different.

As shown in FIG. 1, the mooring anchor 3 is provided on the support parts 2, and after the filter 100 is implanted into the lumen, the mooring anchor 3 penetrates into the tissue of the inner wall of the lumen, and functions to fix the filter 100. It can be appreciated that the embodiments do not limit the specific configuration and placement of the mooring anchor 3, and the mooring anchor 3 may be selectively provided on the guide segment 211 or the support segment 212 so long as the mooring anchor 3 can penetrate into the lumen wall tissue after the filter 100 is implanted into the lumen.

Figure 14:
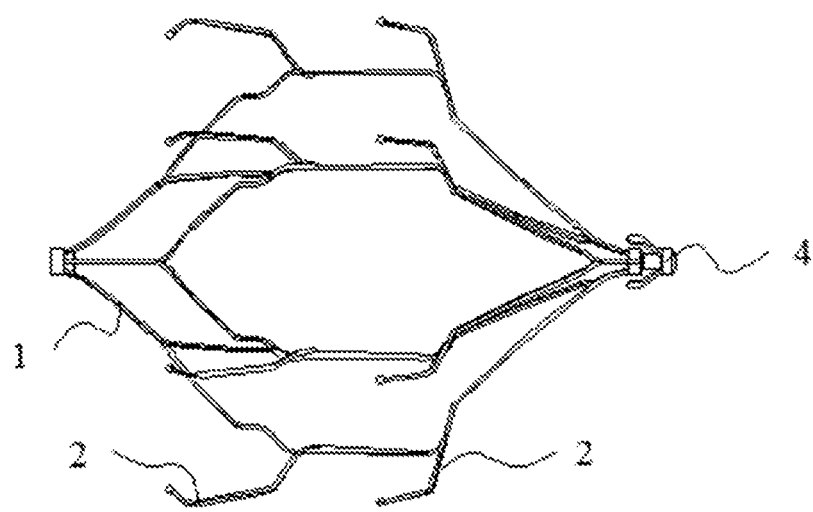
FIG. 14 is a structural schematic diagram that a mooring anchor is not provided on the support parts of the filter shown in FIG. 1.

It can also be appreciated that the mooring anchor 3 may selectively be provided on one or more of the plurality of supports 21, or the mooring anchor 3 may not be provided on the support 21, but the fixation of the filter 100 to the lumen wall may be achieved by the supporting force of the support 21 to the lumen wall, and FIG. 14 shows a schematic diagram of a structure in which no mooring anchor is provided on the support of the filter.

In the present embodiment, two support parts are provided on each connecting segment 132, the two support parts include a first support part connected to the proximal end region of the connecting segments 132, and a second support part connected to the distal end region of the connecting segments 132, and the mooring anchor 3 is provided on the second support part. A distance between the intersection point 20 of the first support part and the connecting segments 132 and the distal end of the bending part 1321 in the direction of the longitudinal center axis of the filter is 0.3 mm-3 mm, and the intersection point of the second support part and the connecting segments 132 is located at the distal end of the connecting segments 132. When a concave structure is provided on the connecting part 1322, the intersection point 20 of the first support part and the connecting segments 132 can be located between the bending part 1321 and the concave structure 1323.

Figure 15:
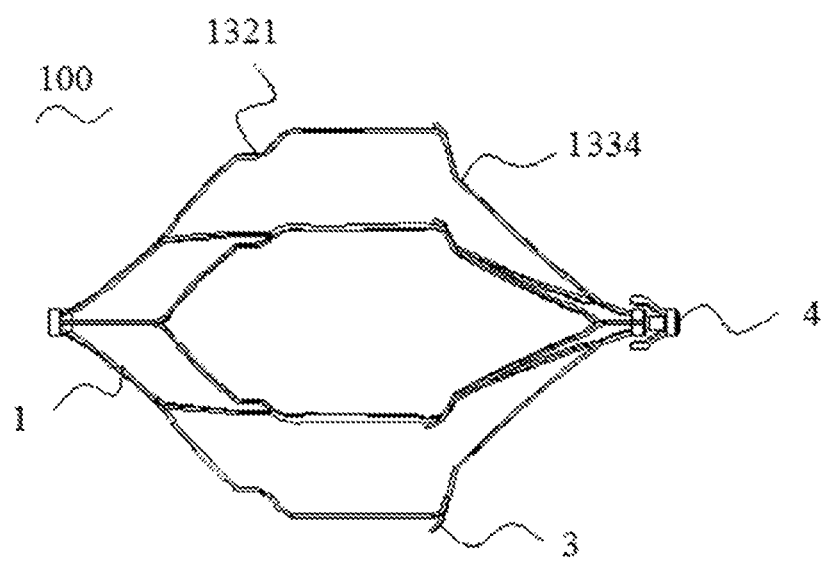
FIG. 15 is a structural schematic diagram of a filter according to another embodiment.

As shown in FIG. 15, the filter according to a second embodiment differs from the first embodiment in that the filter 1 is not provided with the support parts 2, and the mooring anchor 3 is provided directly on the connector 13.

The various features of the above-mentioned embodiments may be combined in any way, and in order to simplify the description, not all possible combinations of the features of the above-mentioned embodiments are described, however, as long as there is no conflict between these features, they should be considered to be within the scope of the description.

The embodiments described above represent only a few embodiments of the present disclosure, the description of which is specific and detailed, but should not be construed to limit the scope. It should be noted that several variations and modifications may be made by those of ordinary skill in the art without departing from the spirit of the present disclosure, which all fall within the scope of the present disclosure.

The invention claimed is:
1. A filter, comprising: a main body part, the main body part comprising a heart-proximal end, a plurality of connecting segments, and a first filter mesh connected between the heart-proximal end and the plurality of connecting segments,
wherein one end, connected to the first filter mesh, of the plurality of connecting segments is bent towards one side of a longitudinal center axis of the filter to form a bending part, and a vertical distance between the proximal end of the bending part and the longitudinal center axis of the filter is less than a vertical distance between the distal end of the bending part and the longitudinal center axis of the filter;
wherein the first filter mesh comprises a plurality of first branch segments, each of the plurality of first branch segments has a distal end away from the heart-proximal end, two adjacent distal ends of the plurality of first branch segments converge to form a distal end of the first filter mesh, and the distal end of the first filter mesh is directly connected to the bending part;
wherein the bending part further comprises a first bending segment and a second bending segment which are connected, the first bending segment is connected between the distal end of the first filter mesh and a proximal end of the second bending segment, the first bending segment comprises a straight segment parallel to the longitudinal center axis of the filter, and a vertical distance between the proximal end of the second bending segment and the longitudinal center axis of the filter is less than a vertical distance between a distal end of the second bending segment and the longitudinal center axis of the filter;
wherein a ratio of a distance between the proximal end of the bending part and the distal end of the bending part in the direction of the longitudinal center axis of the filter to a distance between both ends of each of the plurality of connecting segments in the direction of the longitudinal center axis of the filter is 1/20-3/5; and wherein the main body part further comprises a heart-distal end and a second filter mesh connected between the heart-distal end and the plurality of the connecting segments.

2. The filter according to claim 1, wherein the connecting segments further comprising a connecting part connected between the bending part and the second filter mesh.

3. The filter according to claim 2, wherein a vertical distance between the distal end of the connecting part and the longitudinal center axis of the filter is not less than the vertical distance between the proximal end of the bending part and the longitudinal center axis of the filter, and the vertical distance between the distal end of the connecting part and the longitudinal center axis of the filter is not greater than the vertical distance between the distal end of the bending part and the longitudinal center axis of the filter.

4. The filter according to claim 2, wherein the connecting part is provided with a concave structure.

5. The filter according to claim 2, wherein the second filter mesh is provided with a flexible part bent towards one side of the longitudinal center axis of the filter, and a bending strength of the flexible part is lower than a bending strength of a portion of the second filter mesh other than the flexible part.

6. The filter according to claim 2, wherein the filter further comprises a recovery hook, the recovery hook being provided on the heart-proximal end or the heart-distal end.

7. The filter according to claim 1, wherein the filter further comprises a plurality of support parts connected to the main body part, each of the support parts comprising at least one support.

8. The filter according to claim 7, wherein the at least one support comprises a guide segment connected to one of the plurality of connecting segments, and a support segment connected to the guide segment; and the guide segment extends radially outward towards the heart-proximal end, and the support segment extends radially outward towards the heart-proximal end.

9. The filter according to claim 7, wherein the filter further comprises a mooring anchor, the mooring anchor being connected to the main body part or the support parts.

10. The filter according to claim 1, wherein a ratio of a distance between both ends of the first bending segment in the direction of the longitudinal center axis of the filter to a distance between both ends of the bending part in the direction of the longitudinal center axis of the filter is $1/5$-$3/5$.

11. A filter, comprising: a main body part and a plurality of support parts, the support parts comprising at least one support, the at least one support comprising a guide segment connected to the main body part,
wherein under a natural release state of the filter, an included angle between a connecting line between both ends of the guide segment and a longitudinal center axis of the filter is 20°-85°, and a ratio of a height of the at least one support in a radial direction of the filter to a maximum distance between the at least one support and the longitudinal center axis of the filter is $1/8$-$1/3$;
wherein the main body part comprises a heart-proximal end, a plurality of connecting segments, and a first filter mesh connected between the heart-proximal end and the plurality of connecting segments,
wherein one end, connected to the first filter mesh, of the plurality of connecting segments is bent towards one side of the longitudinal center axis of the filter to form a bending part, and a vertical distance between the proximal end of the bending part and the longitudinal center axis of the filter is less than a vertical distance between the distal end of the bending part and the longitudinal center axis of the filter,
wherein the first filter mesh comprises a plurality of first branch segments, each of the plurality of first branch segments has a distal end away from the heart-proximal end, two adjacent distal ends of the plurality of first branch segments converge to form a distal end of the first filter mesh, and the distal end of the first filter mesh is directly connected to the bending part;
wherein the bending part further comprises a first bending segment and a second bending segment which are connected, the first bending segment is connected between the distal end of the first filter mesh and a proximal end of the second bending segment, the first bending segment comprises a straight segment parallel to the longitudinal center axis of the filter, and a vertical distance between the proximal end of the second bending segment and the longitudinal center axis of the filter is less than a vertical distance between a distal end of the second bending segment and the longitudinal center axis of the filter;
wherein a ratio of a distance between the proximal end of the bending part and the distal end of the bending part in the direction of the longitudinal center axis of the filter to a distance between both ends of each of the plurality of connecting segments in the direction of the longitudinal center axis of the filter is $1/20$-$3/5$; and
wherein the main body part further comprises a heart-distal end and a second filter mesh connected between the heart-distal end and the plurality of the connecting segments.

12. The filter according to claim 11, wherein the filter further comprises a recovery hook, the guide segment extends radially outward toward a side away from the recovery hook, and the guide segment has a support segment connected thereto.

13. The filter according to claim 12, wherein the support segment is a circular arc structure, and the support segment is connected to an end of the guide segment that is away from the recovery hook.

14. The filter according to claim 13, wherein the at least one support further comprises a spherical part connected at an end of a lower folding segment, or the spherical part is connected at an end of the support segment that is away from the guide segment.

15. The filter of claim 12, wherein the main body part further comprises a connector connected between the heart-proximal end and the heart-distal end, and the recovery hook is connected to the heart-proximal end or the heart-distal end.

16. The filter according to claim 15, wherein the connector comprises the first filter mesh connected to the heart-proximal end, the second filter mesh connected to the heart-distal end, and the plurality of connecting segments connected between the first filter mesh and the second filter mesh, the support parts being connected to the connecting segments.

17. The filter according to claim 11, wherein a ratio of a distance between both ends of the first bending segment in the direction of the longitudinal center axis of the filter to a distance between both ends of the bending part in the direction of the longitudinal center axis of the filter is $1/5$-$3/5$.

18. A filter, comprising: a main body part, the main body part comprising a heart-proximal end, a plurality of connecting segments, and a first filter mesh connected between the heart-proximal end and the plurality of connecting segments, wherein one end, connected to the first filter mesh, of the plurality of connecting segments is bent towards one side of a longitudinal center axis of the filter to form a bending part, and a vertical distance between the proximal end of the bending part and the longitudinal center axis of the filter is less than a vertical distance between the distal end of the bending part and the longitudinal center axis of the filter;

wherein the first filter mesh comprises a plurality of first branch segments, each of the plurality of first branch segments has a distal end away from the heart-proximal end, two adjacent distal ends of the plurality of first branch segments converge to form a distal end of the first filter mesh, and the distal end of the first filter mesh is directly connected to the bending part;

wherein the bending part further comprises a first bending segment and a second bending segment which are connected, the first bending segment is connected between the distal end of the first filter mesh and a proximal end of the second bending segment, the first bending segment consists of a straight segment parallel to the longitudinal center axis of the filter, and a vertical distance between the proximal end of the second bending segment and the longitudinal center axis of the filter is less than a vertical distance between a distal end of the second bending segment and the longitudinal center axis of the filter; and wherein the first bending segment is directly connected to the distal end of the first filter mesh.

\* \* \* \* \*